United States Patent [19]

Kojima et al.

[11] 4,418,079
[45] Nov. 29, 1983

[54] CONJUGATED KETONE COMPOUNDS IN PREVENTING PLATELET THROMBOSIS

[75] Inventors: Atsuyuki Kojima; Tsunemasa Irie, both of Hyogo; Shuichi Harada, Osaka; Yoshito Kameno, Osaka; Junki Katsube, Osaka; Hisao Yamamoto, Hyogo, all of Japan

[73] Assignee: Sumitomo Chemical Company, Limited, Osaka, Japan

[21] Appl. No.: 335,522

[22] Filed: Dec. 29, 1981

Related U.S. Application Data

[60] Division of Ser. No. 217,043, Dec. 16, 1980, abandoned, which is a continuation of Ser. No. 973,639, Dec. 27, 1978, abandoned.

[30] Foreign Application Priority Data

Jan. 13, 1978 [JP] Japan ................................. 53-2938
Jan. 13, 1978 [JP] Japan ................................. 53-2939

[51] Int. Cl.³ ............... A61K 27/00; A61K 31/34; A61K 31/36; A61K 31/38; A61K 31/40; A61K 31/44; A61K 31/135; A61K 31/445

[52] U.S. Cl. ................... 424/330; 424/248.4; 424/263; 424/267; 424/274; 424/275; 424/282; 424/285

[58] Field of Search .............. 424/248.4, 263, 267, 424/274, 275, 282, 330, 285

[56] References Cited

U.S. PATENT DOCUMENTS 2,539,801  1/1951  Van Hook ..................... 260/247.7
3,922,266 11/1975  Katsube et al. ................. 260/240 J
3,936,450  2/1976  Mauvernay et al. ............. 424/267
4,012,515  3/1977  Katsube et al. ................. 424/267
4,110,447  8/1978  Gante et al. .................... 424/244

Primary Examiner—Stanley J. Friedman
Attorney, Agent, or Firm—Birch, Stewart, Kolasch & Birch

[57] ABSTRACT

Conjugated ketone compounds of the formula:

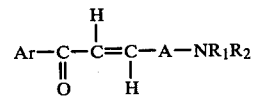

wherein Ar is naphthyl, furyl, thienyl, or phenyl optionally bearing one or more substituents selected from the group consisting of chlorine, bromine, $C_1$–$C_4$ alkyl, $C_1$–$C_4$ alkoxy, $C_1$–$C_4$ alkylthio, trifluoromethyl and methylenedioxy, $R_1$ is $C_1$–$C_6$ alkyl, $C_3$–$C_5$ alkenyl, $C_3$–$C_6$ cycloalkyl, $C_7$–$C_8$ aralkyl or adamantyl, $R_2$ is $C_1$–$C_6$ alkyl, $C_3$–$C_5$ alkenyl or $C_3$–$C_6$ cycloalkyl, or when $R_1$ and $R_2$ are taken together with the nitrogen atom to which they are attached, they form a heterocyclic amino group containing up to 8 carbon atoms, A is straight or branched $C_1$–$C_3$ alkylene, N-[4-(p-chlorophenyl)-4-oxo-2-trans-butenyl]morpholine and N-[4-(p-methoxyphenyl)-4-oxo-2-trans-butenyl]piperidine being excluded, and their non-toxic salts, which are useful as blood platelet anti-aggregative agents.

11 Claims, No Drawings

CONJUGATED KETONE COMPOUNDS IN PREVENTING PLATELET THROMBOSIS

This application is a divisional of copending application Ser. No. 217,043, filed on Dec. 16, 1980, which is a continuation of Ser. No. 973,639, filed on Dec. 27, 1978, both now abandoned.

The present invention relates to conjugated ketone compounds, and their production and use.

The objective conjugated ketone compounds are representable by the formula:

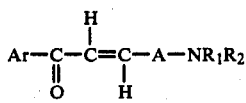

wherein Ar is naphthyl, furyl, thienyl, or phenyl optionally bearing one or more substituents selected from the group consisting of chlorine, bromine, $C_1$–$C_4$ alkyl, $C_1$–$C_4$ alkoxy, $C_1$–$C_4$ alkylthio, trifluoromethyl and methylenedioxy, $R_1$ is $C_1$–$C_6$ alkyl, $C_3$–$C_5$ alkenyl, $C_3$–$C_6$ cycloalkyl, $C_7$–$C_8$ aralkyl or adamantyl, $R_2$ is $C_1$–$C_6$ alkyl, $C_3$–$C_5$ alkenyl or $C_3$–$C_6$ cycloalkyl, or when $R_1$ and $R_2$ are taken together with the nitrogen atom to which they are attached, they form a heterocyclic amino group containing up to 8 carbon atoms and A is straight or branched $C_1$–$C_3$ alkylene. But, N-(p-chlorophenyl-4-oxo-2-trans-butenyl)morpholine and N-[4-(p-methoxyphenyl)-4-oxo-2-trans-butenyl]piperidine are excluded from the objective compounds of this invention.

In the above significances, as "$C_1$–$C_4$ alkyl", there may be exemplified methyl, ethyl, n-propyl, isopropyl, etc. Examples of "$C_1$–$C_4$ alkoxy" are methoxy, ethoxy, n-propoxy, isopropoxy, etc. Examples of "$C_1$–$C_4$ alkylthio" are methylthio, ethylthio, etc. Examples of "$C_1$–$C_6$ alkyl" are methyl, ethyl, n-propyl, isopropyl, n-butyl, isobutyl, n-hexyl, etc. Examples of "$C_3$–$C_5$ alkenyl" are allyl, crotyl, etc. Examples of "$C_3$–$C_6$ cycloalkyl" are cyclopentyl, cyclohexyl, etc. Examples of "$C_7$–$C_8$ aralkyl" are benzyl, phenethyl, etc. Examples of "$C_1$–$C_3$ alkylene" are methylene, ethylene, dimethylmethylene, etc. As the "heterocyclic amino group", there are exemplified pyrrolidino, piperidino, morpholino, isoindolino, 3-azabicyclo[3,2,2]nonanyl, etc.

The conjugated ketone compounds [I] can form acid addition salts (e.g. hydrochlorides, hydrobromides, sulfates, oxalates, citrates, fumarates, maleates, tartrates, etc.), and these salts are also within the scope of this invention.

The conjugated ketone compounds [I] and their non-toxic salts inhibit aggregation of blood platelets and are useful for prevention of intravascular thrombosis, coronary thrombosis, cerebrovascular thrombosis, transient ischemic episodes, and especially for prevention of platelet thrombosis induced by the use of prosthetic devices such as artificial heart valves.

Among the conjugated ketone compounds [I], those of the following formula are preferred:

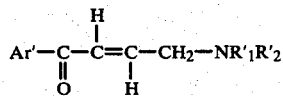

wherein Ar' is naphthyl, furyl, thienyl or phenyl optionally bearing one or more substituents selected from the group consisting of chlorine, bromine, $C_1$–$C_3$ alkyl, methoxy, methylthio, trifluoromethyl and methylenedioxy, $R_1'$ is $C_1$–$C_6$ alkyl, allyl, cyclohexyl, benzyl or adamantyl and $R_2'$ is $C_1$–$C_6$ alkyl, allyl or cyclohexyl, or $NR_1'R_2'$ is pyrrolidino, piperidino, morpholino, 3-azabicyclo[3,2,2]nonanyl or isoindolinyl.

Particularly preferred are those of the formula:

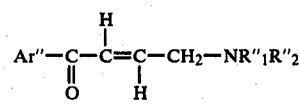

wherein Ar" is naphthyl, furyl, thienyl or phenyl optionally bearing one or more substituents selected from the group consisting of chlorine, bromine, methyl, methoxy, methylthio, trifluoromethyl and methylenedioxy, $R_1''$ is $C_1$–$C_6$ alkyl, cyclohexyl or adamantyl and $R_2''$ is $C_1$–$C_4$ alkyl, or $NR_1''R_2''$ is pyrrolidino, piperidino, 3-azabicyclo[3,2,2]nonanyl or isoindolinyl.

More particularly preferred are those of the formula:

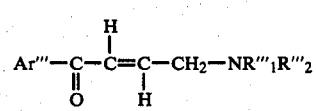

wherein Ar''' is naphthyl, furyl, thienyl or phenyl optionally bearing a substituent selected from the group consisting of chlorine, methyl and methylthio, $R_1'''$ is $C_1$–$C_3$ alkyl, cyclohexyl or adamantyl and $R_2'''$ is $C_1$–$C_3$ alkyl, or $NR_1'''R_2'''$ is pyrrolidino or piperidino.

The conjugated ketone compounds [I] and their non-toxic salts can be administered to warm-blooded animals either alone or in combination with pharmaceutically acceptable carriers. The proportion of the agent administered is determined by the solubility and chemical nature of the compound, chosen route of administration and standard biological practice. For example, they may be administered orally in solid forms, such as tablets or capsules, containing such excipients as starch, milk sugar and so forth. They may be also administered orally in the form of solutions or injected parenterally. For parenteral administration, they may be used in the form of sterile solutions containing other solutes, for example, enough saline or glucose to make the solutions isotonic.

In view of their increased chemical stability and solubility in water, the acid addition salts of the compounds [I] are more suited for the preparation of said pharmaceutical preparations compared with the compounds [I].

The dosage of the active agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.002 mg to about 10 mg per kilogram although as afore-mentioned variations will occur. However, a dosage level in the range of from about 0.01 mg to about 2 mg per kilogram is most satisfactory. Such doses may be administered once to four times a day, as required.

The conjugated ketone compounds [I] can be prepared as shown in the following scheme:

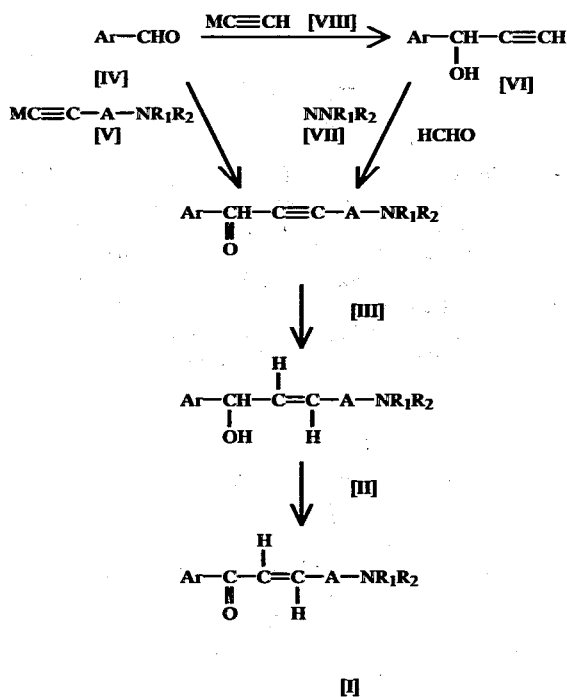

wherein Ar, $R_1$, $R_2$ and A are each as defined above and M is alkali metal or alkaline earth metal halide.

The reaction in the foregoing scheme will be hereinafter illustrated step by step in detail.

Firstly, the acetylenic aryl alcohol [III] is prepared by reacting the aldehyde [IV] with the metal acetylide [V]. The reaction may be conducted by a conventional procedure and is preferably carried out in an inert solvent (e.g. diethyl ether, diisopropyl ether, tetrahydrofuran, dimethoxyethane, hexane, benzene). The reaction can proceed under dry-ice cooling or reflux conditions but is usually effected at room temperature. After the reaction is completed, the desired product may be isolated and purified by a usual manner.

Alternatively, the acetylenic aryl alcohol [III] wherein A is methylene may be prepared by reacting the acetylenic alcohol [VI] with the amine [VII] in the presence of formaldehyde.

The reaction is favorably carried out in the presence of a catalyst in an inert solvent at a temperature from room temperature to reflux of the reaction system. Examples of the solvent are water, methanol, ethanol, isopropanol, isoamyl alcohol, diethyl ether, tetrahydrofuran, dioxane, diethyleneglycol dimethyl ether, ethyleneglycol monomethyl ether, etc. Mixtures thereof are also usable. As the catalyst, there are exemplified cupric chloride, cuprous chloride, cupric sulfate, cuprous acetate, ferric chloride, etc.

In the above reaction, the starting acetylenic alcohol [VI] is obtainable by reacting the aldehyde [IV] with an acetylide [VIII] according to a conventional procedure.

The acetylenic aryl alcohol [III] is then reduced to the trans-olefinic aryl alcohol [II].

This reduction may be accomplished by reacting the acetylenic aryl alcohol [III] with a reducing agent such as a metal hydride (e.g. lithium aluminum hydride, sodium borohydride) or the combination of an alkali metal and an amine (e.g. sodium in liquid ammonia, lithium in methylamine). The reaction using the metal hydride is ordinarily carried out in an inert solvent (e.g. diethyl ether, tetrahydrofuran, dioxane, ethyleneglycol dimethyl ether, benzene, toluene, hexane, cyclohexane) at a temperature from about 0° C. to refluxing temperature. The recovery of the desired product from the reaction mixture may be effected by a usual manner. The olefinic aryl alcohol [II] thus obtained possesses a trans-olefinic double bond.

The trans-olefinic aryl alcohol [II] is then oxidized to the trans-olefinic aryl ketone [I].

The oxidation may be carried out by treating the olefinic aryl alcohol [II] with an oxidizing agent (e.g. manganese dioxide, chromic acid, chromates, permanganates, oxygen, dimethylsulfoxide, peracids), usually in water or an inert organic solvent such as chloroform, dichloromethane, carbon tetrachloride, ethylenedichloride, acetone, methyl ethyl ketone or hexane at room temperature or under cooling or gentle heating. The reaction product is readily separated from the reaction mixture by a conventional procedure.

Pharmacological evaluation has indicated the conjugated ketone compounds [I] of the invention show an anti-aggregative activity for blood platelets.

The aggregometer method of Born [G. V. R. Born: J.Physiol., London, 162, 67 (1962)] as modified by Mustard et al. [J. F. Mustard et al.: J.Lab.Clin.Med., 64, 548 (1964)] was used to assess the in vitro activity of various compounds as to inhibition of collagen and adenosine diphosphate (ADP) induced platelet aggregation. Platelet rich plasma (PRP) was separated by centrifugation from citrated (3.8%) rabbit blood. ADP in final concentration of 10 to 100 μg/ml of a collagen suspension prepared according to the method described by Evans et al. [G. Evans et al.: J.Exp. Med., 128, 877 (1968)] was used to induce aggregation. The test compounds were dissolved in buffer solution so that 0.05 ml added to PRP would yield the desired test concentration. Vehicle control trials were done and compared with aggregation induced in platelet rich plasma containing various concentrations of the test compounds. Dose response curves were obtained, and 50% inhibitive concentration ($IC_{50}$) values were calculated.

TABLE 1

| Compound | | | | | Inhibitory activity $IC_{50}$ (μg/ml) | |
|---|---|---|---|---|---|---|
| No. | Ar | A | $NR_1R_2$ | salt | ADP | Collagen |
| 1 | $C_6H_5$ | $CH_2$ | $N(Me)_2$ | HCl | 3.3 | 2.0 |
| 2 | $C_6H_5$ | $CH_2$ | NMeEt | HCl | 3.0 | 2.2 |
| 3 | $C_6H_5$ | $CH_2$ | $N(Et)_2$ | HBr | 3.3 | 1.5 |
| 4 | $C_6H_5$ | $CH_2$ | $N(n-Pr)_2$ | HCl | 2.5 | 1.3 |
| 5 | $C_6H_5$ | $CH_2$ | $N(iso-Pr)_3$ | HCl | 3.7 | 1.6 |
| 6 | $C_6H_5$ | $CH_2$ | $N(n-Bu)_2$ | HCl | 5.2 | 2.7 |

TABLE 1-continued

| Compound No. | Ar | A | NR₁R₂ | salt | Inhibitory activity IC$_{50}$ (μg/ml) ADP | Collagen |
|---|---|---|---|---|---|---|
| 7 | C₆H₅ | CH₂ | NMe(1-Ad) | HCl | 3.6 | 2.4 |
| 8 | C₆H₅ | CH₂ | NMe(cyclo-Hex) | HCl | 1.8 | 3.7 |
| 9 | C₆H₅ | CH₂ | 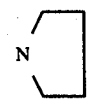 | HCl | 2.5 | 1.2 |
| 10 | C₆H₅ | CH₂ | 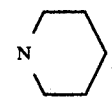 | HCl | 5.2 | 3.2 |
| 11 | C₆H₅ | (CH₂)₂ | N(Et)₂ | HCl | 6.0 | 1.8 |
| 12 | 2-Cl—C₆H₄ | CH₂ | N(Et)₂ | HCl | 3.1 | 2.8 |
| 13 | 3-Cl—C₆H₄ | CH₂ | 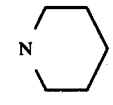 | HCl | 3.1 | 3.1 |
| 14 | 4-Cl—C₆H₄ | CH₂ | N(Et)₂ | HCl | 1.6 | 2.5 |
| 15 | 4-Cl—C₆H₄ | CH₂ | 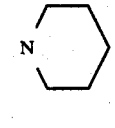 | HCl | 4.8 | 1.6 |
| 16 | 4-Br—C₆H₄ | CH₂ | 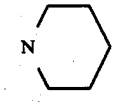 | HCl | 3.2 | 3.0 |
| 17 | 4-Me—C₆H₄ | CH₂ | N(Et)₂ | HCl | 2.3 | 1.5 |
| 18 | 4-Me—C₆H₄ | CH₂ | 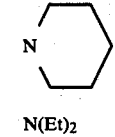 | HCl | 2.0 | 3.4 |
| 19 | 4-MeO—C₆H₄ | CH₂ | N(Et)₂ | HCl | 3.7 | 3.5 |
| 20 | 3,4-(OCH₂O)—C₆H₃ | CH₂ | N(Et)₂ | HCl | 1.3 | 3.7 |
| 21 | 2-MeS—C₆H₄ | CH₂ | 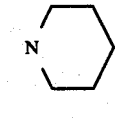 | HCl | 3.2 | 3.7 |
| 22 | 4-MeS—C₆H₄ | CH₂ | N(Me)₂ | HCl | 1.2 | 2.2 |
| 23 | 4-MeS—C₆H₄ | CH₂ | N(Et)₂ | HCl | 1.4 | 2.4 |
| 24 | 4-MeS—C₆H₄ | CH₂ | N(n-Pr)₂ | HCl | 3.6 | 2.6 |
| 25 | 4-MeS—C₆H₄ | CH₂ | 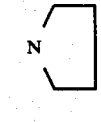 | HCl | 3.0 | 1.1 |
| 26 | 4-MeS—C₆H₄ | CH₂ | 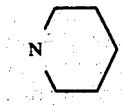 | HCl | 1.2 | 1.5 |
| 27 | 2-CF₃—C₆H₄ | CH₂ | N(Et)₂ | HCl | 3.0 | 4.2 |
| 28 | 4-CF₃—C₆H₄ | CH₂ | 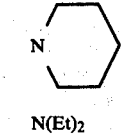 | HCl | 2.7 | 3.1 |
| 29 | β-Naphthyl | CH₂ | N(Et)₂ | HCl | 1.25 | 1.7 |

TABLE 1-continued

| Compound No. | Ar | A | NR₁R₂ | salt | Inhibitory activity IC$_{50}$ (μg/ml) ADP | Collagen |
|---|---|---|---|---|---|---|
| 30 | β-Naphthyl | CH₂ | (N-cyclohexyl ring) | HCl | 2.2 | 2.2 |
| 31 | 2-Furyl | CH₂ | N(Et)₂ | HCl | 3.0 | 1.8 |
| 32 | 2-Furyl | CH₂ | NMe(n-Hex) | HCl | 4.5 | 5.8 |
| 33 | 2-Furyl | CH₂ | (N-cyclohexyl ring) | HCl | 3.8 | 2.2 |
| 34 | 2-Thienyl | CH₂ | N(Et)₂ | HCl | 3.0 | 2.3 |
| 35 | 2-Thienyl | CH₂ | (N-cyclohexyl ring) | HCl | 2.8 | 1.8 |
| 36 | C₆H₅ | CH₂ | (N-cyclopentyl ring) | HCl | 2.7 | 1.2 |
| Papaverine |   |   |   |   | 65 | 60 |

Notes:
Me, methyl; Et, ethyl; Pr, propyl; Bu, butyl; Ad, 1-adamantyl; Cyclo-Hex, cyclohexyl; n-Hex, n-hexyl.

The conjugated ketone compounds [I] were also tested ex vivo in rats where ADP or collagen was used to induce aggregation in PRP samples obtained 1 hour after oral administration. Blood was drawn after dosing and the procedure of platelet aggregation was the same as the in vitro experiments. Inhibitory values were calculated compared with the activity of PRP samples of vehicle treated rats. The dose required to produce 50% inhibition of the aggregation (ED$_{50}$) was determined by dose response data obtained in this manner. For instance, compound No. 3 had an ED$_{50}$ of 0.3 mg/kg (ADP) and 3 mg/kg (collagen). Further, for instance, compound No. 10 had an ED$_{50}$ of 2 mg/kg (collagen).

The conjugated ketone compounds [I] are superior blood platelet anti-aggregative agents to the conjugated ketone derivatives as disclosed in U.S. Pat. No. 4,012,515 in many respects. The compounds as disclosed in that patent are the α,β-unsaturated derivatives of the so-called "butyrophenone neuroleptics", which possessed potent neuroleptic activities. Compared with such compounds, the compounds [I] of this invention show increased blood platelet anti-aggregative activity with smaller or no neuroleptic properties. For instance, the typical α,β-unsaturated ketone derivative in the said patent is the one of the formula:

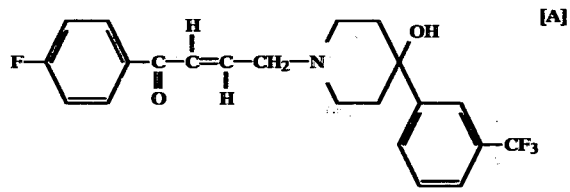

Compound No. 3 as a typical compound of this invention is more potent than the compound [A] in blood platelet anti-aggregation activity and does not produce any slight degree of neuroleptic activity. Thus, Compound No. 3 possesses fewer side effects and is more specific and intensive in its activity.

The summary of the pharmacological test results is shown in Table 2.

TABLE 2

| Compound No. | Neuroleptic activity (Anti apomorphine test*) ED$_{50}$ (rat, s.c., mg/kg) | Blood platelet aggregation inhibitory activity IC$_{50}$ (in vitro, μg/ml) ADP | Collagen |
|---|---|---|---|
| 3 | No effect at 10 mg/kg | 3.3 | 1.5 |
| A | 0.1 | 9.0 | 3.5 |

Note:
*P. A. J. Janssen et al.: Arzneimittel-Forschung, 15, 104–117 (1965)

The following examples are given for the purpose of illustration only, and it is not intended to limit the invention thereby.

EXAMPLE 1

N-(4-Phenyl-4-oxo-2-trans-butenyl)-N,N-diethylamine hydrobromide (a) N,N-Diethylpropargylamine To a solution of diethylamine (104.5 g) in anhydrous benzene (240 ml) was added dropwise a solution of propargyl bromide (85.0 g) in anhydrous benzene (140 ml) with stirring at a temperature below 10° C., and the resulting mixture was stirred at 40° to 45° C. for 3 hours. After filtration of precipitates, the filtrate was concentrated in order to remove a large portion of benzene under atmospheric pressure. The residual oil was extracted with 10% aqueous solution of hydrochloric acid, and the extract was neutralized with 10% aqueous solution of sodium hydroxide to separate an oily liquid. The liquid was dried over potassium carbonate and distilled to afford N,N-diethylpropargylamine, b.p., 120°–121° C./760 mmHg.

(b) 1-Phenylpropargyl alcohol

A solution of ethyl magnesium bromide in anhydrous tetrahydrofuran, prepared from magnesium (33.0 g) in tetrahydrofuran (200 ml) and ethyl bromide (172.0 g) in tetrahydrofuran (400 ml) in a conventional manner, was added to a solution of acetylene (72 g) in anhydrous tetrahydrofuran (1600 ml) at −30° to −20° C. for 50 minutes, and the resulting solution was stirred at a temperature below 0° C. for 50 minutes. To the resulting solution was added a solution of benzaldehyde (106.1 g) in anhydrous tetrahydrofuran (100 ml) with stirring at 0° to 10° C. for 1 hour, and stirring was continued at room temperature for 1 day. After water was added to the solution with stirring under ice-cooling and precipitates were filtered off, the filtrate was evaporated, and the residual oil was distilled to afford 1-phenyl-propargyl alcohol, b.p., 120°–121° C./17 mmHg.

(c) N-(4-Phenyl-4-hydroxy-2-butynyl)-N,N-diethylamine (First method: Grignard reaction)

To a solution of ethyl magnesium bromide in anhydrous ether, prepared from magnesium (584 mg) in ether (25 ml) and ethyl bromide (3.00 g) in ether (5 ml) in a conventional manner, was added a solution of N,N-diethyl propargylamine (2.70 g) in anhydrous tetrahydrofuran (8 ml) with stirring at room temperature, and the resulting mixture was stirred under reflux for 30 minutes. To the resulting solution was added dropwise a solution of benzaldehyde (2.54 g) in anhydrous tetrahydrofuran (7 ml) at a temperature below 10° C., and the mixture was stirred at room temperature for 2 hours. The cooled reaction mixture was diluted with ethyl acetate (50 ml), and water was added thereto in order to decompose metal complexes. The reaction mixture was dried over sodium sulfate and filtered. The filtrate was evaporated and chromatographed to afford N-(4-phenyl-4-hydroxy-2-butynyl)-N,N-diethylamine, b.p., 134°–137° C./0.12 mmHg. M.P., 52°–53.5° C.

(Second method: Mannich reaction)

To a solution of 1-phenylpropargyl alcohol (119.12 g) in dioxane (650 ml), a solution of diethylamine (99.2 g) in water (300 ml), a solution of 37% formalin (148.9 g) in dioxane (200 ml) and a solution of cupric sulfate (pentahydrate) (8.11 g) in water (180 ml) were added with stirring at room temperature. The resulting mixture was stirred at about 70° C. for 2 hours and then filtered off, and the filtrate was evaporated under reduced pressure. The residual oily material was dissolved in benzene (450 ml) and extracted with three 300 ml portions of 5% aqueous solution of hydrochloric acid, and the extracts were combined together and washed with benzene (300 ml). The washed extract was neutralized with an aqueous solution of sodium hydroxide and extracted with three 400 ml portions of chloroform, and the extracts were washed with water (500 ml) and dried over sodium sulfate. The chloroform-extracts were evaporated and then distilled to afford N-(4-phenyl-4-hydroxy-2-butynyl)-N,N-diethylamine, b.p., 134°–137° C./0.12 mmHg.

(d) N-(4-Phenyl-4-hydroxy-2-trans-butenyl)-N,N-diethylamine

To an ethereal solution (1000 ml) of lithium aluminum hydride (57.0 g) was added a solution of N-(4-phenyl-4-hydroxy-2-butynyl)-N,N-diethylamine (164.05 g) in ether (500 ml) with stirring under ice-cooling for 1.5 hours, and then stirring was continued for 5 hours at room temperature. Water was added to the cooled reaction mixture in order to decompose excess lithium aluminum hydride. The precipitates were filtered, and the filtrate was evaporated and distilled to afford N-(4-phenyl-4-hydroxy-2-trans-butenyl)-N,N-diethylamine, b.p., 116°–120° C./0.12 mmHg.

(e) N-(4-Phenyl-4-oxo-2-trans-butenyl)-N,N-diethylamine hydrobromide

To a solution of N-(4-phenyl-4-hydroxy-2-trans-butenyl)-N,N-diethylamine (44.04 g) in chloroform (1000 ml), manganese dioxide (350 g) was added portionwise with stirring at 15° to 20° C. for 10 minutes, and stirring was continued for 3 hours under ice-cooling. After filtration of inorganic materials, the filtrate was evaporated to afford N-(4-phenyl-4-oxo-2-trans-butenyl)-N,N-diethylamine, which formed its hydrobromide with a solution of hydrogen bromide (16.3 g) in anhydrous ether (200 ml), m.p., 92°–94° C.

In the same manner as in Example 1, the following compounds were obtained:

| Ar | A | NR$_1$R$_2$ | Salt | M.P. (°C.) |
| --- | --- | --- | --- | --- |
| C$_6$H$_5$ | CH$_2$ | N(Me)$_2$ | HCl | 128–129 |
| C$_6$H$_5$ | CH$_2$ | NMeEt | HCl | 108–110 |
| C$_6$H$_5$ | CH$_2$ | N(Et)$_2$ | HBr | 92–94 |
| C$_6$H$_5$ | CH$_2$ | N(n-Pr)$_2$ | HCl | 107–108 |
| C$_6$H$_5$ | CH$_2$ | N(iso-Pr)$_2$ | HCl | 109–111 |
| C$_6$H$_5$ | CH$_2$ | N(n-Bu)$_2$ | HCl | 93—94 |
| C$_6$H$_5$ | CH$_2$ | N(iso-Bu)$_2$ | HCl | 110–111 |
| C$_6$H$_5$ | CH$_2$ | N(n-Hex)$_2$ | HCl | 87–89 |
| C$_6$H$_5$ | CH$_2$ | NMe(1-Ad) | HCl | 165–166 |
| C$_6$H$_5$ | CH$_2$ | NMe(cyclo-Hex) | HCl | 166–168 |
| C$_6$H$_5$ | CH$_2$ | NBzl(cyclo-Hex) | HCl | 148–149 |
| C$_6$H$_5$ | CH$_2$ |  | HCl | 136–138 |

-continued
| Ar | A | NR₁R₂ | Salt | M.P. (°C.) |
|---|---|---|---|---|
| C₆H₅ | CH₂ |  | HCl | 147–148 |
| C₆H₅ | CH₂ |  | HCl | 149–150 |
| C₆H₅ | CH₂ | 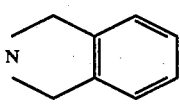 | HCl | 159–160 |
| C₆H₅ | CH₂ |  | HCl | 176.5–177.5 |
| C₆H₅ | (CH₂)₂ | N(Et)₂ | HCl | 113–115 |
| C₆H₅ | C(Me)₂ | N(Me)₂ | HCl | 142–143.5 |
| 2-Cl—C₆H₄ | CH₂ | N(Et)₂ | HCl | 106–108 |
| 2-Cl—C₆H₄ | CH₂ |  | HCl | 129,5–132.5 |
| 3-Cl—C₆H₄ | CH₂ |  | HCl | 151–152 |
| 4-Cl—C₆H₄ | CH₂ | N(Et)₂ | HCl | 121–122 |
| 4-Cl—C₆H₄ | CH₂ |  | HCl | 171.5–172.5 |
| 4-Br—C₆H₄ | CH₂ |  | HCl | 156–157.5 |
| 4-Me—C₆H₄ | CH₂ | N(Et)₂ | HCl | 141–142 |
| 4-Me—C₆H₄ | CH₂ |  | HCl | 163–164 |
| 4-(iso-Pr)—C₆H₄ | CH₂ |  | HCl | 170.5–171 |
| 4-MeO—C₆H₄ | CH₂ | N(Et)₂ | HCl | 147–148 |
| 3,4,5-tri(MeO)—C₆H₂ | CH₂ |  | HCl | 157.5–158.5 |
| 3,4-(OCH₂O)—C₆H₃ | CH₂ | N(Et)₂ | HCl | 144–145 |

-continued

| Ar | A | NR₁R₂ | Salt | M.P. (°C.) |
|---|---|---|---|---|
| 2-MeS—C₆H₄ | CH₂ | piperidino | HCl | 146–147 |
| 4-MeS—C₆H₄ | CH₂ | N(Me)₂ | HCl | 138–140 |
| 4-MeS—C₆H₄ | CH₂ | N(Et)₂ | HCl | 143–144 |
| 4-MeS—C₆H₄ | CH₂ | N(n-Pr)₂ | HCl | 124–125 |
| 4-MeS—C₆H₄ | CH₂ | N(iso-Bu)₂ | HCl | 133–134 |
| 4-MeS—C₆H₄ | CH₂ | N(Allyl)₂ | (COOH)₂ | 113–115 |
| 4-MeS—C₆H₄ | CH₂ | pyrrolidino | HCl | 131–132 |
| 4-MeS—C₆H₄ | CH₂ | piperidino | HCl | 151.5–152.5 |
| 2-CF₃—C₆H₄ | CH₂ | N(Et)₂ | HCl | 78–80 |
| 4-CF₃—C₆H₄ | CH₂ | piperidino | HCl | 162–162.5 |
| β-Naphthyl | CH₂ | N(Et)₂ | HCl | 122.5–123.5 |
| β-Naphthyl | CH₂ | piperidino | HCl | 157–157.5 |
| β-Naphthyl | CH₂ | morpholino | HCl | 153–154 |
| 2-Furyl | CH₂ | N(Et)₂ | HCl | 133–134 |
| 2-Furyl | CH₂ | NMe(n-Hex) | HCl | 115–116.5 |
| 2-Furyl | CH₂ | piperidino | HCl | 154.5–155.5 |
| 2-Thienyl | CH₂ | N(Et)₂ | HCl | 120–122 |
| 2-Thienyl | CH₂ | NMe(n-Hex) | HCl | 127–128.5 |
| 2-Thienyl | CH₂ | piperidino | HCl | 150–152. |

Notes:
Me, methyl; Et, ethyl; Pr, propyl; Bu, butyl; Hex, hexyl; Ad, 1-adamantyl; Cyclo-Hex, cyclohexyl; Bzl, benzyl.

What is claimed is:

1. A method for the prevention of platelet thrombosis which comprises administering to warm-blooded animals an effective blood platelet anti-aggregative amount of at least one compound of the formula

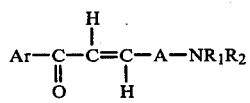

wherein Ar is naphthyl, furyl, thienyl or phenyl optionally bearing one or more substituents selected from the group consisting of chlorine, bromine, $C_1$–$C_4$ alkyl, $C_1$–$C_4$ alkoxy, $C_1$–$C_4$ alkylthio, trifluoromethyl and methylenedioxy, $R_1$ is $C_1$–$C_6$ alkyl, $C_3$–$C_5$ alkenyl, $C_3$–$C_6$ cycloalkyl, $C_7$–$C_8$ aralkyl or adamantyl, $R_2$ is $C_1$–$C_6$ alkyl, $C_3$–$C_5$ alkenyl or $C_3$–$C_6$ cycloalkyl, or when $R_1$ and $R_2$ are taken together with the nitrogen atom to which they are attached, they form a heterocyclic amino group containing up to 8 carbon atoms, A is straight or branched $C_1$–$C_3$ alkylene, N-[4-(p-chlorophenyl)-4-oxo-2-trans-butenyl]morpholine and N-[4-(p-methoxyphenyl)-4-oxo-2-trans-butenyl]piperidine being excluded or a non-toxic salt thereof and at least one pharmaceutically acceptable inert carrier or diluent.

2. The method of claim 1, wherein Ar is naphthyl, furyl, thienyl or phenyl optionally bearing one or more substituents selected from the group consisting of chlorine, bromine, $C_1$-$C_3$ alkyl, methoxy, methylthio, trifluoromethyl and methylenedioxy, $R_1$ is $C_1$-$C_6$ alkyl, allyl, cyclohexyl, benzyl or adamantyl and $R_2$ is $C_1$-$C_6$ alkyl, allyl or cyclohexyl, or $NR_1R_2$ is pyrrolidino, piperidino, morpholino, 3-azabicyclo[3,2,2]nonanyl or isoindolinyl.

3. The method of claim 2, wherein Ar is naphthyl, furyl, thienyl or phenyl optionally bearing one or more substituents selected from the group consisting of chlorine, bromine, methyl, methoxy, methylthio, trifluoromethyl and methylenedioxy, $R_1$ is $C_1$-$C_6$ alkyl, cyclohexyl or adamantyl and $R_2$ is $C_1$-$C_4$ alkyl, or $NR_1R_2$ is pyrrolidino, piperidino, 3-azabicyclo[3,2,2]nonanyl or isoindolinyl.

4. The method of claim 3, wherein Ar is naphthyl, furyl, thienyl or phenyl optionally bearing a substituent selected from the group consisting of chlorine, methyl and methylthio, $R_1$ is $C_1$-$C_3$ alkyl, cyclohexyl or adamantyl and $R_2$ is $C_1$-$C_3$ alkyl, or $NR_1R_2$ is pyrrolidino or piperidino.

5. The method of claim 1, wherein Ar is unsubstituted naphthyl or phenyl or a naphthyl or phenyl group having one or more substituents selected from the group consisting of chlorine, bromine, $C_1$-$C_4$ alkyl, $C_1$-$C_4$ alkoxy, $C_1$-$C_4$ alkylthio and trifluoromethyl, $R_1$ is $C_1$-$C_6$ alkyl, $C_3$-$C_5$ alkenyl, $C_3$-$C_6$ cycloalkyl, $C_7$-$C_8$ aralkyl or adamantyl, $R_2$ is $C_1$-$C_6$ alkyl, $C_3$-$C_5$ alkenyl or $C_3$-$C_6$ cycloalkyl.

6. The method of claim 5, wherein Ar is unsubstituted phenyl or a phenyl group having one or more substituents selected from the group consisting of chlorine, bromine, $C_1$-$C_4$ alkyl, $C_1$-$C_4$ alkoxy, $C_1$-$C_4$ alkylthio, and trifluoromethyl.

7. The method of claim 5, wherein Ar is unsubstituted phenyl or a phenyl group having one or more substituents selected from the group consisting of chlorine, bromine, methyl, methoxy, methylthio and trifluoromethyl, $R_1$ is $C_1$-$C_6$ alkyl, allyl, cyclohexyl, benzyl or adamantyl and $R_2$ is $C_1$-$C_6$ alkyl, allyl or cyclohexyl.

8. The method of claim 7, wherein Ar is unsubstituted phenyl or a phenyl group having one or more substituents selected from the group consisting of chlorine, methyl and methylthio, $R_1$ is $C_1$-$C_3$ alkyl, cycloalkyl or adamantyl and $R_2$ is $C_1$-$C_3$ alkyl.

9. The method of claim 8, wherein Ar is phenyl.

10. The method of claim 5, wherein said compound is N-(4-phenyl-4-oxo-2-trans-butenyl)N,N-diethylamine.

11. The method of claim 5, wherein Ar is unsubstituted phenyl or a phenyl group having one or more trifluoromethyl substituents, $R_1$ is $C_1$-$C_6$ alkyl or adamantyl and $R_2$ is $C_1$-$C_6$ alkyl.

* * * * *